US012800495B2

(12) United States Patent
Shkolnikov et al.

(10) Patent No.: US 12,800,495 B2
(45) Date of Patent: Nov. 17, 2026

(54) FLUORESCENCE DETECTION VIA LIGHT GUIDE

(71) Applicant: Hewlett-Packard Development Company, L.P., Spring, TX (US)

(72) Inventors: Viktor Shkolnikov, Palo Alto, CA (US); Alexander Govyadinov, Corvallis, OR (US)

(73) Assignee: HEWLETT-PACKARD DEVELOPMENT COMPANY, L.P., Spring, TX (US)

( * ) Notice: Subject to any disclaimer, the term of this patent is extended or adjusted under 35 U.S.C. 154(b) by 444 days.

(21) Appl. No.: 18/564,526

(22) PCT Filed: May 28, 2021

(86) PCT No.: PCT/US2021/034750
§ 371 (c)(1),
(2) Date: Nov. 27, 2023

(87) PCT Pub. No.: WO2022/250685
PCT Pub. Date: Dec. 1, 2022

(65) Prior Publication Data
US 2024/0288368 A1 Aug. 29, 2024

(51) Int. Cl.
*G01N 21/64* (2006.01)
*G01N 21/03* (2006.01)
(Continued)

(52) U.S. Cl.
CPC ..... *G01N 21/6428* (2013.01); *G01N 21/0332* (2013.01); *G01N 21/05* (2013.01);
(Continued)

(58) Field of Classification Search
CPC .......... G01N 21/6428; G01N 21/0332; G01N 21/05; G01N 21/645; G01N 33/5005;
(Continued)

(56) References Cited

U.S. PATENT DOCUMENTS 6,438,279 B1 8/2002 Craighead et al.
7,521,179 B2 4/2009 Bachi
(Continued)

FOREIGN PATENT DOCUMENTS

WO 2010/112495 A1 10/2010

*Primary Examiner* — Michael L Hobbs
(74) *Attorney, Agent, or Firm* — FOLEY & LARDNER LLP

(57) ABSTRACT

In one example in accordance with the present disclosure, a fluorescence detection system is described. The fluorescence detection system includes a microfluidic chamber to receive a sample containing a compound to be detected. The system also includes a light guide, a portion of which is adjacent the microfluidic chamber. The light guide refracts excitation light into the microfluidic chamber to excite fluorophores in the microfluidic chamber. The light guide has total internal reflection in those portions that are not adjacent the microfluidic chamber. The fluorescence detection system also includes a heating element to trigger a reaction in the microfluidic chamber, an illumination source to provide the excitation, and a detection system to detect fluorescence generated by the excitation of the fluorophores in the microfluidic chamber.

15 Claims, 19 Drawing Sheets

(51) Int. Cl.
*G01N 21/05* (2006.01)
*G01N 33/50* (2006.01)

(52) U.S. Cl.
CPC . *G01N 33/5005* (2013.01); *G01N 2021/0325* (2013.01); *G01N 2021/052* (2013.01); *G01N 2201/0636* (2013.01); *G01N 2201/0638* (2013.01); *G01N 2201/0806* (2013.01)

(58) Field of Classification Search
CPC ........... G01N 33/49; G01N 2021/0325; G01N 2021/052; G01N 2021/0636; G01N 2021/0638; G01N 2021/0806; G01N 2021/0346; G01N 2021/6439; G01N 2021/6482
See application file for complete search history.

(56) References Cited

U.S. PATENT DOCUMENTS

| | | | |
|---|---|---|---|
| 8,325,342 B2 | 12/2012 | Ali et al. | |
| 9,777,317 B2 | 10/2017 | Spoto et al. | |
| 2008/0149840 A1 | 6/2008 | Handique et al. | |
| 2009/0140170 A1 | 6/2009 | Nevill et al. | |
| 2012/0020840 A1 | 1/2012 | Craig | |
| 2014/0219871 A1* | 8/2014 | Sjolander ............... | G01N 21/05 422/69 |
| 2017/0100718 A1 | 4/2017 | Tan et al. | |
| 2020/0056229 A1* | 2/2020 | Mir .................... | G01N 21/6428 |

* cited by examiner

FLUORESCENCE DETECTION VIA LIGHT GUIDE

CROSS-REFERENCE TO RELATED APPLICATIONS

This application is a U.S. National Stage Patent Application under 35 U.S.C. § 371 of PCT/US2021/034750, filed May 28, 2021, which is hereby incorporated by reference in its entirety.

BACKGROUND

Cellular biology is a field of biology that studies the structure, function, and operation of cells. An understanding of the structure, function, and operation of cells provides a wealth of information. For example, individual cells may be used to generate cell lines and to aide in the further understanding of mechanisms of cellular function. As another example, once the structure, function, and operation of cells is more fully understood, certain diseases may be prevented and treated.

BRIEF DESCRIPTION OF THE DRAWINGS

The accompanying drawings illustrate various examples of the principles described herein and are part of the specification. The illustrated examples are given merely for illustration, and do not limit the scope of the claims.

Throughout the drawings, identical reference numbers designate similar, but not necessarily identical, elements.

Figure 1:
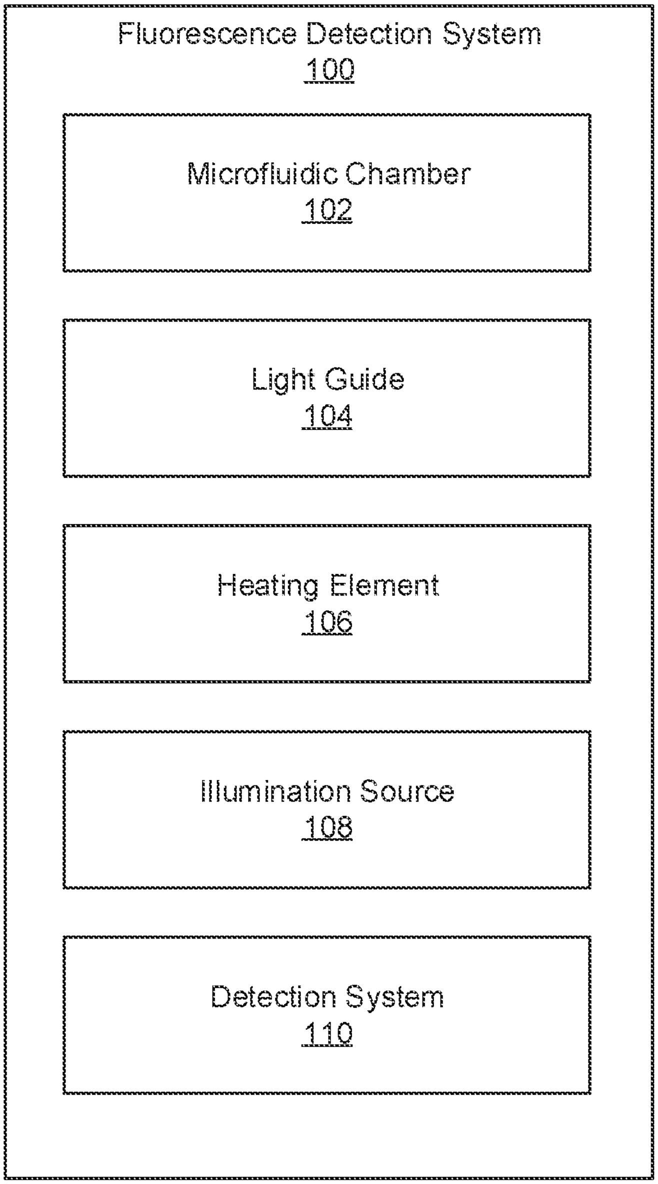
FIG. 1 is a block diagram of a light guide fluorescence detection system, according to an example of the principles described herein.

The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

Cellular biology is a field of biology that studies the structure, function, and operation of cells. With an understanding of the structure, function, and operation of cells, a variety of chemical reactions and processes can be carried out. For example, individual cells may be used to generate additional cells, perform genetic testing, and identify infection agents. A wealth of information can be collected from a cellular sample. A greater understanding of the different kinds of cells and their function can lead to technological innovations. For example, certain biologics such as proteins, insulin, other therapeutic drugs, ribonucleic acid (RNA), and deoxyribonucleic acid (DNA) may be obtained.

In one particular example, scientists may conduct a polymerase chain reaction (PCR) to generate high quantities of deoxyribonucleic acid (DNA) on which studies are performed. PCR makes millions to billions of copies of a specific DNA sample. As such, a scientist may take a small sample of DNA and amplify it to a large number of copies, such that it may be studied in detail. During PCR, a sample is quickly heated to around 100 degrees Celsius (C) and then cooled to around 50 degrees C. This process is repeated tens of times. While operations such as PCR greatly enhance the ability of scientists to carry out a variety of experiments, some advancements to devices that carry out PCR may further increase its efficacy and use in scientific laboratories and doctors' offices. For example, nucleic acid detection is helpful as a way to diagnose infection diseases. A more accurate infectious disease diagnosis, including a more sensitive diagnosis and better differential diagnosis, may be possible via a device that performs with a higher rate of detection.

To provide the more accurate infectious disease diagnosis and to provide more control and insight for a chemical reaction, the present specification describes a system for accurately tracking a chemical reaction. For example, digital microfluidic devices may be digital droplet microfluidic devices where a droplet generator generates droplets and simultaneously packs reagents into the droplets, which droplets are used as micro reaction chambers. An example of such an operation is digital droplet PCR. In another example, droplets with reagents are manipulated using electrowetting phenomena to perform chemical operations. In either example, tracking of the droplets ensures that the assay is executing as desired. That is, droplet tracking provides feedback control over the reaction such that the reaction may be adjusted to be more efficient. Secondly, enhanced illumination of the particles in a reaction enhances the overall signal-to-noise ratio (SNR). Selective illumination enhances the SNR by avoiding illuminating areas where no compounds of interest are present and thereby avoids the scattering of light from those areas into the detector. Moreover, with enhanced illumination, more fluorophores are available to absorb an excited photon and emit an emission photon. Thus, the system produces more emission photons and so has a higher signal.

In many cases, droplet tracking is done by tracking fluorescence of a target compound. Optical fluorescence occurs when a molecule absorbs light at wavelengths within its absorption band, and then emits light at longer wavelengths within its emission band. For compound tracking, fluorescing molecules referred to as fluorophores are attached to biological molecules and other targets of interest to enable identification, quantification, and even real-time observation of biological and chemical activity. While tracking fluorescence allows the tracking of a chemical reaction, some advancements may provide for more efficient fluorescence tracking. For example, it may be that the excitation light which is provided to excite the fluorophores is lost in a reaction chamber. Moreover, excitation of a fluorophore produces emission light that is omnidirectional, such that much of the emission light is not directed towards a detection system that tracks the reaction.

Accordingly, the present specification describes a microfluidic chamber to enhance the rate of capture of the fluorescence signal. Specifically, the system includes a light guide and a microfluidic chamber adjacent the light guide. The light guide directs an excitation light towards the microfluidic chamber. The ratio of refractive indices of ambient air and the light guide material defines a critical angle and produces total internal reflection for light rays that have an incidence angle greater than the critical angle such that a greater portion of excitation light remains within the light guide. However, when the excitation light passes through a zone of the light guide that is adjacent the microfluidic chamber, the index of refraction ratio between the light guide and the microfluidic chamber is such that total internal reflection is broken, i.e., the critical angle increases, and the excitation light is directed to the microfluidic chamber. That is, the excitation light is maintained within the light guide until it passes through a portion of the light guide that is adjacent the microfluidic chamber. As such, less light is lost to the environment and is instead preserved and directed to the microfluidic chamber.

In some examples, the present system also includes components to increase the capture rate of the fluorescence. For example, the fluorescence detection system may include a reflective coating on the microfluidic chamber to prevent lost emission light.

As a greater amount of light is maintained within the fluorescence detection system, a less intense light may be used. That is, if the excitation light is too powerful it may bleach, or otherwise degrade, the compounds in the microfluidic chamber. As a higher percentage of excitation light and emission light is captured, a less intense excitation light source may be used, which reduces the rate of bleaching of the compounds. Moreover, as more emission light is directed to the detection system, greater accuracy regarding the detected reaction is ensured.

Specifically, the present specification describes a fluorescence detection system. The fluorescence detection system includes a microfluidic chamber to receive a sample containing a compound to be detected and a light guide. A portion of the light guide is adjacent the microfluidic chamber. The light guide 1) is to refract excitation light into the microfluidic chamber to excite fluorophores in the microfluidic chamber and 2) has a critical angle in portions not adjacent the microfluidic chamber that is smaller than a critical angle in portions adjacent the microfluidic chamber. The fluorescence detection system also includes a heating element to trigger a reaction in the microfluidic chamber, an illumination source to provide the excitation light; and a detection system to detect fluorescence generated by the excitation of the fluorophores in the microfluidic chamber.

The present specification also describes a method. According to the method, excitation light is introduced into a light guide of a fluorescence detection system. The excitation light is refracted towards a microfluidic reaction chamber adjacent the light guide. A reaction is triggered within the microfluidic chamber. This may be done by heating a sample within the microfluidic chamber. The reaction is monitored by 1) exciting, with the excitation light, fluorophores within the microfluidic chamber such that the fluorophores fluoresce and 2) detecting, at a detection system, the fluorophores that are indicative of a target compound within the microfluidic chamber.

In another example, the fluorescence detection system includes a longitudinal microfluidic chamber to receive a sample containing a compound to be detected and a longitudinal light guide having a first portion adjacent the longitudinal microfluidic chamber and a second portion not adjacent the longitudinal microfluidic chamber. As before, the light guide is to refract excitation light into the adjacent longitudinal microfluidic chamber along the first portion and has a smaller critical angle in portions not adjacent the microfluidic chamber than the critical angle in portions adjacent the microfluidic chamber. The fluorescence detection system includes a heating element disposed between the longitudinal microfluidic chamber and the longitudinal light guide to trigger a reaction in the longitudinal microfluidic chamber and an illumination source at one end of the longitudinal microfluidic chamber to provide the excitation light to the longitudinal microfluidic chamber. An excitation filter between the illumination source and the longitudinal light guide allows the excitation light to pass and filters light not absorbed by the fluorophores. The fluorescence detection system also includes a detection system at an opposite end of the longitudinal microfluidic chamber to detect fluorescence generated by the excitation of the compounds in the microfluidic chamber. An emission filter between the longitudinal light guide and the detection system allows an emission light to pass and filters the excitation light.

As such, the fluorescence detection system of the present specification increases the fluorescence within a microfluidic chamber and captures an increased amount of emitted fluorescence such that a reaction, such as a PCR, may be run more efficiently. Specifically, the system of the present specification includes an embedded heater and light guide to collect a large fraction of light emitted by fluorescence indicators transducing a nucleic acid detection reaction. In some examples this may be facilitated by surrounding the microfluidic chamber with a mirror to direct the emission light towards the detection system.

Note that while the present specification describes particular types of target compounds or particles, the present systems and methods may target and eject other types of compounds and particles including beads of various materials such as metal and latex, DNA-functionalized beads, and other microspheres.

In summary, such a fluorescence detection system 1) provides a higher signal to noise ratio for compound detection; 2) reduces the computational resources to perform accurate compound detection; 3) provides for faster compound detection to facilitate higher fidelity and faster feedback control; and 4) enables higher speed droplet assays. However, the devices disclosed herein may address other matters and deficiencies in a number of technical areas.

Further, as used in the present specification and in the appended claims, the term "a number of" or similar language is meant to be understood broadly as any positive number including 1 to infinity.

Also, as used in the present specification and in the appended claims, the term "angle of incidence" or "incident angle" refers to an angle between a light ray incident on a surface and a line perpendicular to the surface at the point of incidence, called the normal.

Still further, as used in the present specification and in the appended claims, the term "critical angle" refers to an angle of incidence beyond which rays of light passing through a denser medium to the surface of a less dense medium are no longer refracted but totally reflected, (i.e., total internal reflection TIR)).

Turning now to the figures, FIG. 1 is a block diagram of a light guide fluorescence detection system (100), according to an example of the principles described herein. In some examples, the fluorescence detection system (100) may be a microfluidic structure. In other words, the chamber (102) may be a microfluidic structure. A microfluidic structure is a structure of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

As described above, the fluorescence detection system (100) may be used to detect compounds and particles of a variety of types. For example, the fluorescence detection system (100) may be implemented in a life science application. Accordingly, a biological fluid may be analyzed and/or passed by the fluorescence detection system (100).

As a specific example, the fluorescence detection system (100) may be used to count cells in a particular sample fluid. The fluorescence detection system (100) may be part of a larger fluid ejection system. For example, the fluorescence detection system (100) may be implemented in a laboratory and may pass a sample to other components of the larger system.

The sample analyzed by the fluorescence detection system (100) may be of a variety of types and may be used for a variety of applications. In some examples, the biological fluid may include solvent or aqueous-based pharmaceutical compounds, as well as aqueous-based biomolecules including proteins, enzymes, lipids, antibiotics, mastermix, primer, DNA samples, cells, or blood components, all with or without additives, such as surfactants or glycerol.

The fluorescence detection system (100) includes a microfluidic chamber (102) to receive a sample containing a compound to be detected. In some examples, such as those depicted in subsequent figures, the microfluidic chamber (102) may be a cylindrical chamber. However, the microfluidic chamber (102) may have a variety of cross-sectional areas and configurations.

In an example, the microfluidic chamber (102) holds fluid to be statically heated and cooled. That is, fluid is introduced into a microfluidic chamber (102) where the fluid rests while the heating element (106) cyclically heats and cools it. Once the reaction or scientific operation is complete, the microfluidic chamber (102) may be separated, for example removed and discarded, while an output of the reaction is recorded by the detection system (110) and analyzed.

In another example, the microfluidic chamber (102) is a channel through which the fluid is to flow. The fluid flow through the microfluidic channel may be generated by a pump that is disposed upstream or downstream from the reaction portion of the microfluidic chamber (102). In some examples, the pump may be an integrated pump, meaning the pump is integrated into a wall of the microfluidic channel. In some examples, the pump may be an inertial pump which refers to a pump which is in an asymmetric position within the microfluidic channel. In some examples, the pump may be a thermal inkjet resistor, or a piezo-drive membrane or any other displacement device.

The fluorescence detection system (100) also includes a light guide (104) to direct the excitation light towards the microfluidic chamber (102) where a reaction is to occur. Specifically, a portion of the light guide (104) is adjacent the microfluidic chamber (102) whereas a portion, such as portions before and after the microfluidic chamber (102) in a direction of excitation light travel, are not adjacent the microfluidic chamber (102). The material properties of the light guide (104) and the air surrounding light guide (104) may be such that the light guide (104) has total internal reflection at a lower critical angle in portions not adjacent the microfluidic chamber (102). The total internal reflection may be broken, that is the critical angle at which total internal reflection occurs may increase, as the excitation light enters a portion of the light guide (104) that is adjacent the microfluidic chamber (102).

Total internal reflection is a phenomenon where light in a medium is reflected back into the medium so long as the angle of incidence of light impinging on the interface is greater than a "critical" angle. The critical angle at which total internal reflection is exhibited is based on the index of refraction of each medium at an interface between the two mediums. For example, prior to reaching a portion of the light guide (104) adjacent the microfluidic chamber (102), the interface may be a light guide (104)/air interface. In an example, the light guide may be formed of an optically transparent material such as acrylic, glass, or cyclic-olefin-copolymer (COC. As a particular example, air may have a refractive index of 1, and COC may have a refractive index of 1.49. As such, the critical angle at this interface may be arcsin (1/1.49)=42°. That is, light rays having greater than a 42° incident angle at the COC/air interface will be contained in the light guide (104). As the illumination source (108) may be parallel to the light guide (104), this may indicate that the majority of excitation light remains in the light guide (104) when adjacent ambient air.

By comparison, water in the microfluidic chamber (102) may have a refractive index of 1.333. As such, the critical angle at this interface may be arcsin (1.33/1.49)=63°, which is a greater critical angle than the critical angle at the light guide/air interface. That is, light rays having greater than a 63° incident angle at the COC/water interface will be contained in the light guide (104). By comparison, the portion of rays that impinge the COC/water interface at an incident angle lower than 63° will be directed into the microfluidic chamber (102) where they may excite fluorophores to generate a detectable signal.

As such, the total internal reflection may be "broken" meaning that the critical angle increases such that more light is refracted into the microfluidic chamber (102) and less light is maintained within the COC light guide (104). Put another way, as the critical angle at the COC/water interface is greater than the critical angle at the COC/air interface (e.g., 63° as compared to 42°), more light will have an incidence angle less than the critical angle at the COC/water interface. Therefore, more light will be refracted through the COC/water into the microfluidic chamber (102) than is refracted through the COC/air interface.

By comparison, the critical angle of the microfluidic chamber/air interface may be arcsin (1/1.33)=49° given the ratio of refractive indices between the microfluidic chamber (102) water (n=1.33) and air (n=1). As such, any light that hits this interface with an angle greater than 49 degrees would be reflected back into the microfluidic chamber (102).

As such, the light guide (104) material may be selected to have a comparable or lower refractive index than the water in the microfluidic chamber (102). In a particular example, the ratio of refractive indices between the light guide (104) and the microfluidic chamber (102) may be between 1.05 and 2.5. As such, prior to reaching the section of light guide (104) adjacent the microfluidic chamber (102), a first portion of excitation light guided into the light guide (104) bounces off the walls of the light guide (104) due to total internal reflection and is not lost to air due to the lower index of refraction of the air. However, an amount of this first portion of the excitation light escapes into the microfluidic chamber (102) portion due to the microfluidic chamber (102) refractive index, thus exciting the fluorophores within the microfluidic chamber (102).

The fluorescence detection system (100) also includes a heating element (106) to trigger a reaction within the microfluidic chamber (102). That is, some reactions, such as PCR, are triggered by the cycling heating of a sample with a target compound. Accordingly, the heating element (106) may be formed of a resistive material such as indium tin oxide (ITO), tin (IV) oxide ($SnO_2$), zinc tin oxide (ZTO), or aluminum zinc oxide among others. In some examples, the heating element (106) may be formed of these or other transparent resistive materials. In some examples, the heating element (106) may be fabricated in the form of a thin film deposited by physical or chemical vapor deposition, among other manufacturing techniques.

The fluorescence detection system (100) further includes an illumination source, such as a light-emitting diode (LED). The illumination source (108) provides the excitation light provided to the microfluidic chamber (102) to excite the fluorophores such that a reaction may be tracked. The excitation light may come in a variety of wavelengths. For example, the excitation light may be ultraviolet having a wavelength of between 350 and 400 nanometers. However, excitation light with other wavelengths light may be provided by the illumination source (108). For example, the excitation light may be in the infrared wavelength range.

The fluorescence detection system (100) may also include a detection system (110) to detect the fluorescence. That is, as described above, when exposed to the excitation light, the fluorophores may fluoresce and emit a light, which emitted light may have a longer wavelength than the excitation light. For example, the emission band may have a wavelength of between 400 and 459 nanometers.

The detection system (110) may include an array of light sensitive components to detect the light emitted from the fluorophores. For example, the detection system (110) may include a charge coupled device (CCD) or a complementary metal-oxide semiconductor (CMOS) device, both of which are image sensors that detect light. In another example, the detection system (110) may be a point detector such as a photodiode.

In either example, as fluorescence emits from a target compound in the microfluidic chamber (102), it is directed towards the detection system (110). The characteristics, i.e., quantity and quality, of received fluorescence allows a user to track the reaction. For example, the degree of emission light that is detected may be used to indicate the degree of amplification of a target compound and/or a quantity of target compound in the microfluidic chamber. Accordingly, the present fluorescence detection system (100) identifies target particles in a sample by 1) increasing the amount of excitation light to excite the fluorophores and 2) increasing the rate of emitted light incidence upon the detection system (110).

Figure 2A:
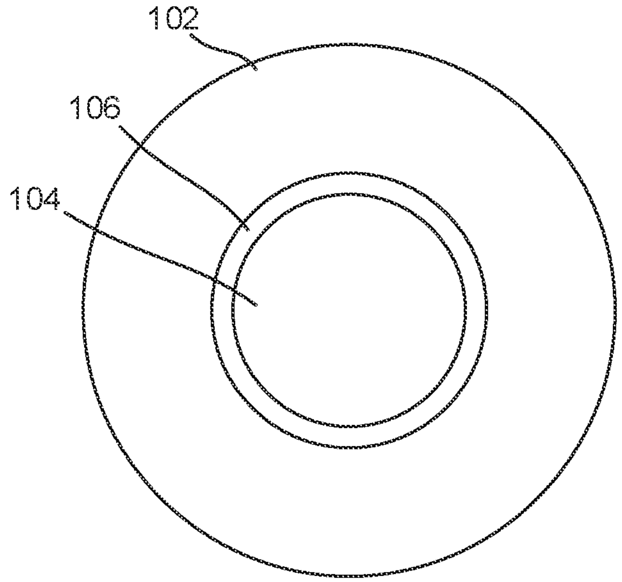
FIGS. 2A and 2B are diagrams of a light guide fluorescence detection system, according to an example of the principles described herein.
Figure 2B:
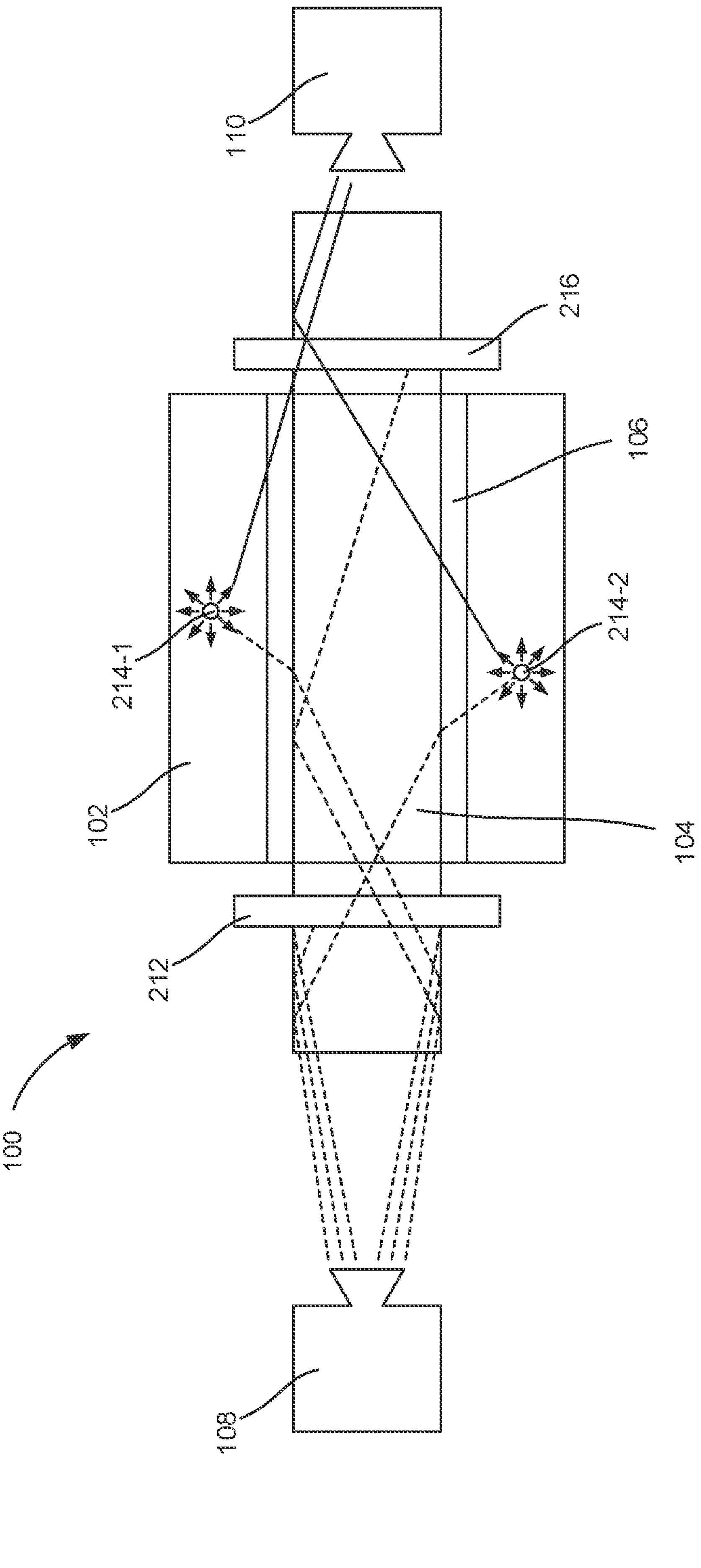

FIGS. 2A and 2B are diagrams of a fluorescence detection system (FIG. 1, 100), according to an example of the principles described herein. Specifically, FIG. 2A is a cross-sectional view of the microfluidic chamber (102), heating element (106), and light guide (104) and FIG. 2B is a side view of the fluorescence detection system (FIG. 1, 100).

As depicted in FIG. 2A, in some examples the microfluidic chamber (102) surrounds the light guide (104). In such an example, the heating element (106) may be a transparent resistive material such as indium tin oxide or aluminum zinc oxide such that the excitation light may pass from the light guide (104), through the heating element (106), and towards the microfluidic chamber (102) to interact with the fluorophores therein.

FIG. 2B is a side view of the fluorescence detection system (100) depicted in FIG. 2A. As described above, the microfluidic chamber (102) and the light guide (104) may be longitudinal. The light guide (104) may have a first portion which is adjacent, and in this case surrounded by, the microfluidic chamber (102). The light guide (104) may have a second portion, for example on either side of the first portion, that is not adjacent the microfluidic chamber (102). As described above, the illumination source (108) may be at one end of the longitudinal light guide (104) to provide excitation light (depicted in dashed lines) to the light guide (104). Due to the illumination source (108) being in line with the light guide (104) and due to the ratio of refractive indexes between the light guide (104) and ambient air in the second portion, a majority of the excitation light may not strike the interface at an angle greater than the critical angle and is thus reflected to remain in the light guide (104) in the second portion.

In this example, the fluorescence detection system (100) further includes an excitation filter (212) between the illumination source (108) and the longitudinal light guide (104) to allow the excitation light to pass and to filter light not absorbed by the fluorophores (214-1, 214-2). The excitation filter (212) may be a bandpass filter that passes the wavelengths absorbed by the fluorophore and filters other wavelengths, thus reducing excitation of other sources of fluorescence. In one example, the excitation range may be ultraviolet (UV) or infrared (IR). However, other ranges of excitation light may be filtered by the excitation filter (212). Table (1) provides a table of fluorophores and their respective excitation and emission wavelengths. In this example, an excitation filter (212) and emission filter (216) may be a band pass filter with a range+/−20 nanometers around the identified values.

TABLE 1

| Fluorophore | Excitation wave-length | Emission wave-length |
|---|---|---|
| Dilithium 6-amino-2-(hydrazinecarbonyl)-1,3-dioxo-2,3-dihydro-1H-benzo[de]isoquinoline-5,8-disulfonate | 428 nm | 544 nm |
| 2-(4-Amidinophenyl)-1H-indole-6-carboxamidine | 359 nm | 461 nm |
| N,N-bis(2-chloroethyl)-4-[3-[6-[6-(4-methylpiperazin-1-yl)-1H-benzimidazol-2-yl]-1H-benzimidazol-2-yl]propyl]aniline | 352 nm | 455 nm |
| Propidium iodide | 300 nm | 610 nm |
| 4-(3-amino-6-imino-4,5-disulfoxanthen-9-yl)benzene-1,3-dicarboxylic acid | 555 nm | 585 nm |
| 4-(2,5-dioxopyrrolidin-1-yl)oxycarbonyl-2-[7,7,19,19-tetramethyl-9,17-bis(sulfomethyl)-2-oxa-6,20-diazapentacyclo[12.8.0.03,12.05,10.016,21]docosa-1(14),3,5,8,10,12,15,17,21-nonaen-13-yl]benzoic acid | 580 nm | 600 nm |

TABLE 1-continued

| Fluorophore | Excitation wave-length | Emission wave-length |
|---|---|---|
| monomeric red fluorescent protein (mCherry) | 587 nm | 610 nm |
| Green fluorescent protein (GFP) | 480 nm | 500 nm |

Once past the excitation filter (212), total internal reflection is broken. That is, the ratio between the index of refraction of the light guide (104) and the material in the microfluidic chamber (102) is such that the critical angle is increased and more excitation light is refracted, into the microfluidic chamber (102). That is, due to the ratio of refractive indices of the sample in the microfluidic chamber (102) and the light guide (104), once an excitation light wave hits an interface with the microfluidic chamber (102), the excitation light rays enter the microfluidic chamber (102). Accordingly, the total internal reflection is locally disrupted, allowing for light to cross the interface.

As the excitation light enters the microfluidic chamber (102), it interacts with and excites fluorophores (214-1, 214-2) that are adhered to a target compound. When excited, the fluorophore emits omnidirectional emission light (indicated in solid lines). Note that for simplicity, the figures of the present specification depict a few lines representing light rays. The emitted light may have a longer wavelength, for example between 400 and 440 nanometers.

The fluorescence detection system (100) may also include an emission filter (216) between the longitudinal light guide (104) and the detection system (110) to allow an emission light to pass and filter the excitation light. Similar to the excitation filter (212), the emission filter (216) may be a band pass or long pass filter to allow the longer wavelength emission light to pass, while filtering the excitation light from being detected by the detection system (110). Once past the emission filter (216), total internal reflection is again re-established at the lower critical angle (i.e., 42° as opposed to 63°), such that more light within the light guide (104) is maintained therein to be directed to the detection system (110).

Figure 3A:
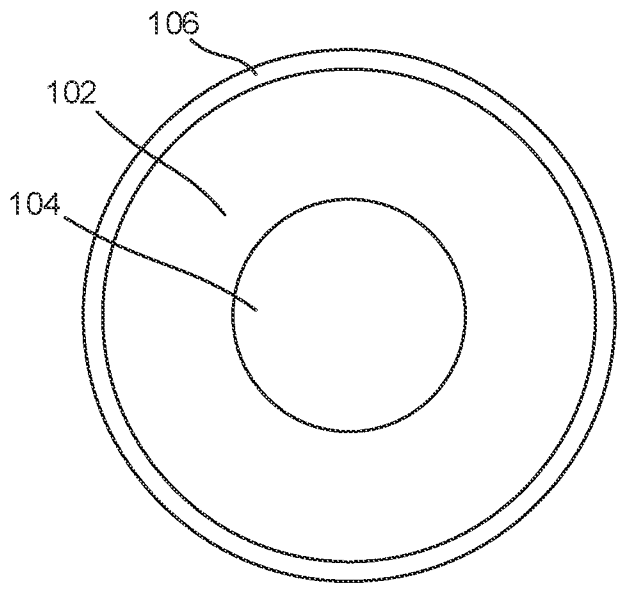
FIGS. 3A and 3B are diagrams of a light guide fluorescence detection system, according to an example of the principles described herein.
Figure 3B:
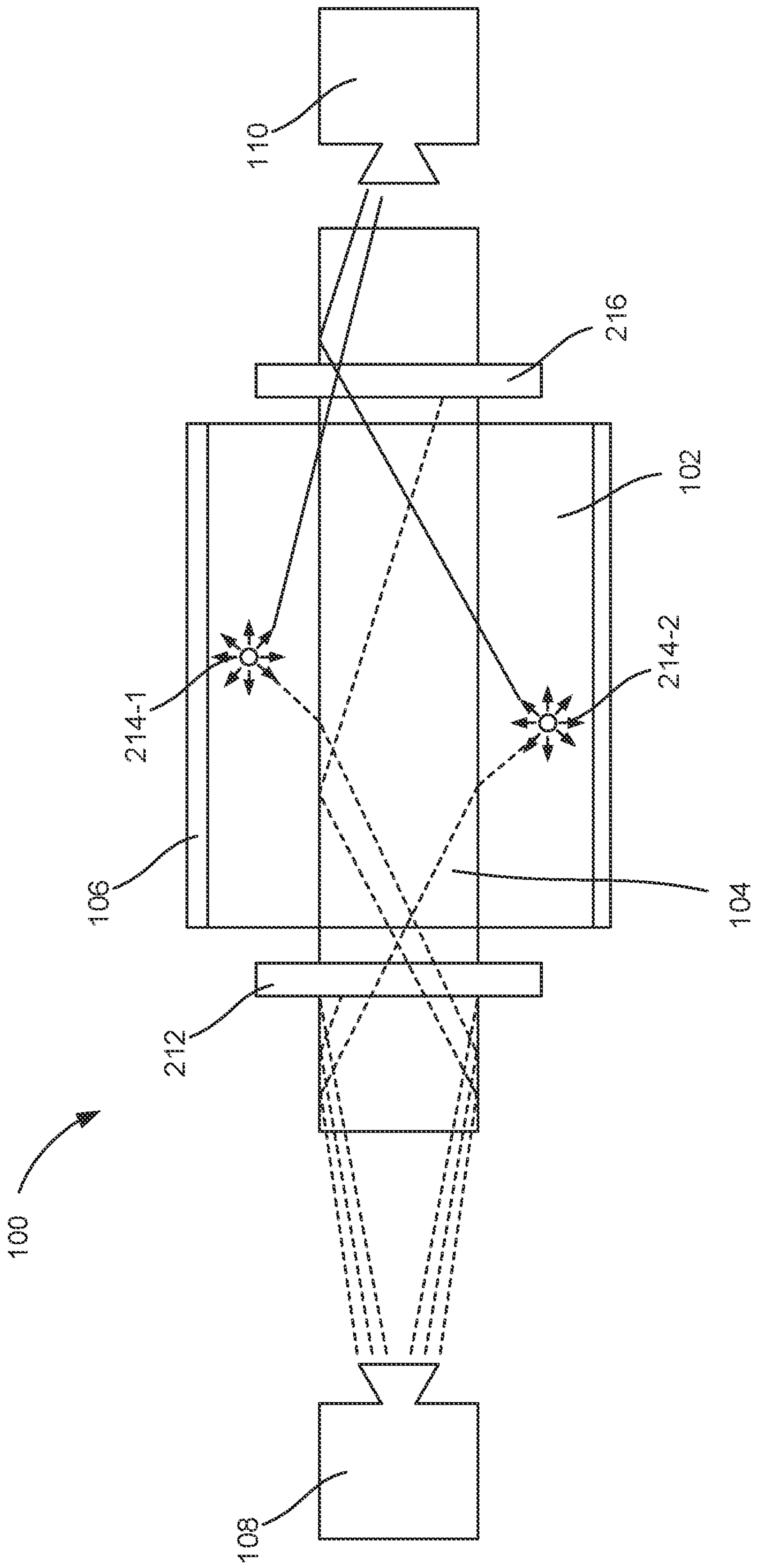

FIGS. 3A and 3B are diagrams of a fluorescence detection system (FIG. 1, 100), according to an example of the principles described herein. In the example depicted in FIGS. 3A and 3B, the heating element (106) is disposed around the microfluidic chamber (102). The heating element (106) disposed on an exterior of the microfluidic chamber (102) may be formed out of transparent resistive material. In another example, the external heating element (106) may be formed of a non-transparent resistive material such as nichrome, platinum, gold, tantalum, polysilicon, conductive carbon, manganese oxide, ruthenium oxide, tungsten silicon carbide, and other electrically conductive materials.

Figure 4A:
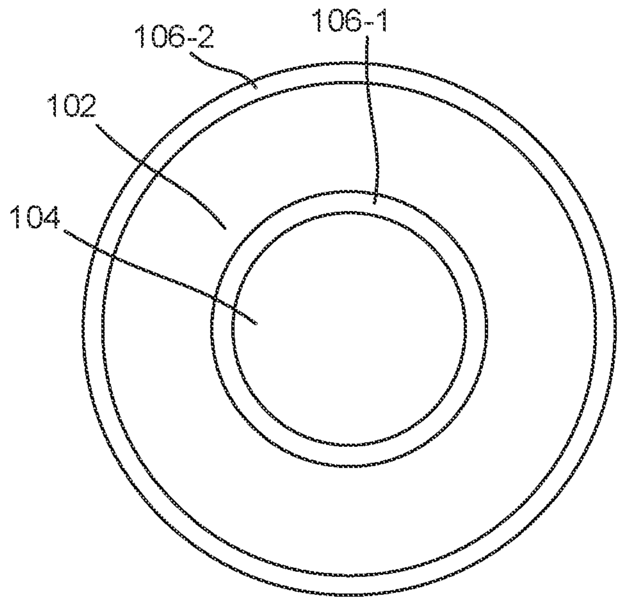
FIGS. 4A and 4B are diagrams of a light guide fluorescence detection system, according to an example of the principles described herein.
Figure 4B:
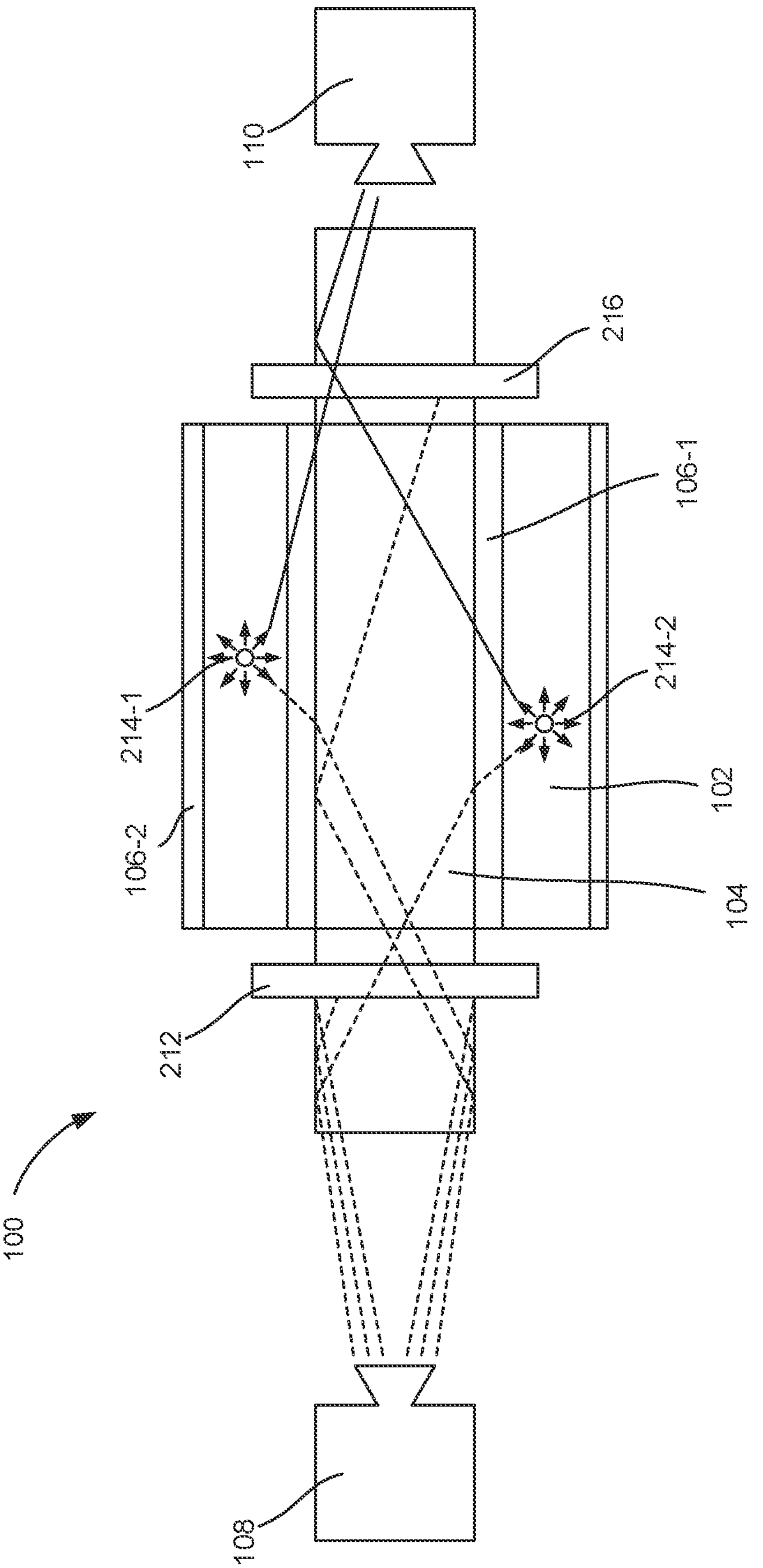

FIGS. 4A and 4B are diagrams of a fluorescence detection system (FIG. 1, 100), according to an example of the principles described herein. In the example depicted in FIGS. 4A and 4B, the system (FIG. 1, 100) includes a second heating element (106-2) that surrounds the microfluidic chamber (102). In this example, the first heating element (106-1) may be transparent while the second heating element (106-2) may be transparent or opaque. A multi-heating element (106) fluorescence detection system (FIG. 1, 100) may provide increased thermal control over the reaction. That is, heat boundary conditions may be set by controlling the first and second heating elements (106-1, 106-2) such that a precise temperature inside the microfluidic chamber (102) may be maintained. When performing thermal cycling, such as in PCR, greater control over the heating and cooling of the sample may reduce the overall time to process a sample. That is, by heating the sample from multiple sides, the fluorescence detection system (FIG. 1, 100) can heat and cool sample to desired temperatures in less time, with more uniform temperature distributions, and with less waste heat entering the ambient system.

Figure 5:
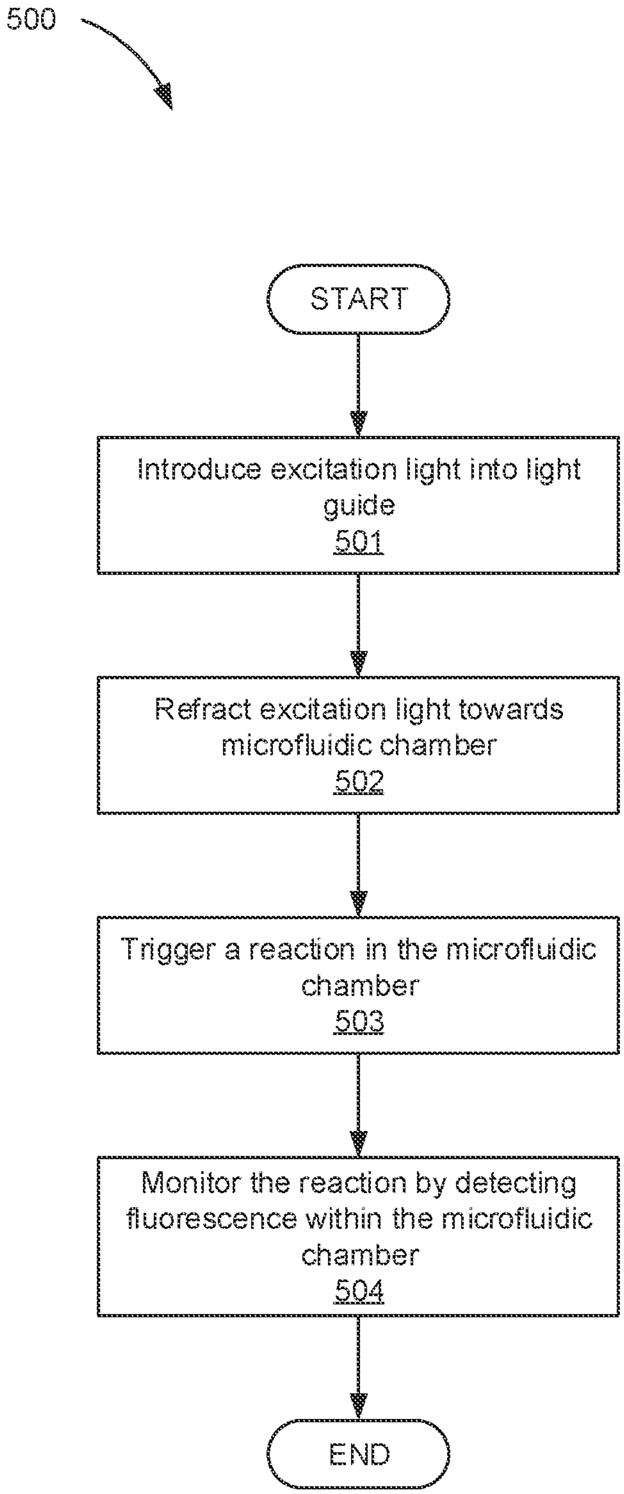
FIG. 5 is a flowchart of a method for detecting a compound via a light guide fluorescence detection system, according to an example of the principles described herein.

FIG. 5 is a flowchart of a method (500) for detecting compounds via a fluorescence detection system (FIG. 1, 100), according to an example of the principles described herein. According to the method (500), an excitation light is introduced (block 501) into a light guide (FIG. 1, 104) of a fluorescence detection system (FIG. 1, 100). As described above, the illumination source (FIG. 1, 108) may be in line with the light guide (FIG. 1, 104) such that the excitation light introduced remains in the light guide (FIG. 1, 104) via total internal reflection. As the excitation light passes a portion of the light guide (FIG. 1, 104) that is adjacent a microfluidic chamber (FIG. 1, 102), which has a different refractive index than air, the total internal reflection is broken, that is, the critical angle increases such that more light is refracted, and specifically refracted (block 502) towards the microfluidic reaction chamber (FIG. 1, 102) adjacent the light guide (FIG. 1, 104). A reaction is then triggered (block 503) in the microfluidic chamber (FIG. 1, 102) by heating the sample within the microfluidic chamber (FIG. 1, 102).

Specifically, the method (500) may be used in a PCR operation. During a PCR operation, a scientist may introduce a PCR master mix and a target DNA sample into the microfluidic chamber (FIG. 1, 102). During PCR, the fluid in the fluid chamber (FIG. 1, 102) is cyclically heated and cooled, first to a temperature to separate the DNA into single strands. Accordingly, a current is sent to a heating element (FIG. 1, 106). Responsive to this current, the resistor heats up and changes the temperature of the fluid, for example to around 100 C.

The temperature of the device is then sensed using a thermal sense resistor. When a target temperature is reached, that is when a temperature is reached that results in the DNA separating, the current is turned off to allow the fluid to cool, for example to around 50 C. During this cooling period, DNA primers attach to the separated strands of DNA. It is then determined if this was the last cycle. If not, the process repeats. For example, in PCR the fluid may be heated again to allow the replicated DNA strands to be extended by the polymerase in the PCR master mix. Accordingly, one PCR run has 3 phases, denaturing, annealing, and extending. This process of denaturing, annealing, and extending may be performed between 20-40 times to create a large sample from the target DNA sample. If it was the last cycle, that is, if each of the cycles of multiple PCR runs have been performed, the process ends.

The reaction may be monitored (block 504) throughout by exciting the fluorophores within the microfluidic chamber (FIG. 1, 102) such that the fluorophores fluoresce and detecting (block 505) the fluorescence that is indicative of a target compound within the microfluidic chamber (FIG. 1, 102). That is, fluorophores may be adhered to strands of DNA such that a quantity of detected fluorescence may indicate the amplification process of the PCR. As such, the amount of fluorescence detected is indicative of the stage or degree of amplification. Such data may be used to track the progress and efficacy of a particular PCR reaction.

Figure 6A:
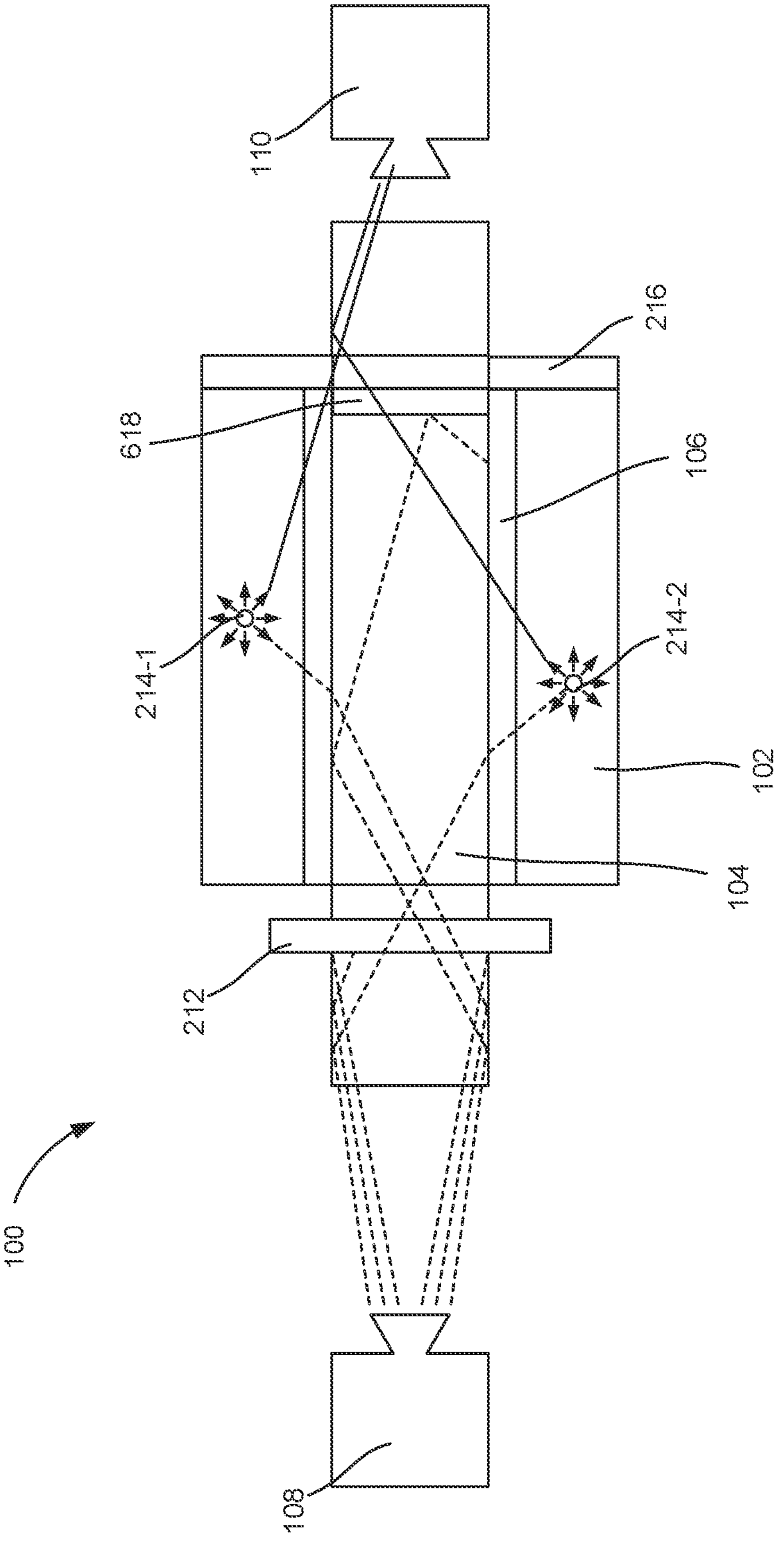
FIGS. 6A and 6D are diagrams of a light guide fluorescence detection system, according to an example of the principles described herein.

FIGS. 6A through 6D are diagrams of a fluorescence detection system (100), according to an example of the principles described herein. As depicted in FIG. 6A, in some examples, the fluorescence detection system (100) may include a reflective element (618) adjacent the emission filter (216) to reflect the excitation light towards the microfluidic chamber (102). In this example, the reflective element (618) may align with the longitudinal light guide (104) and the emission filter (216) may be a ring filter surrounding the reflective element (618).

The reflective element (618) may take a variety of forms. For example, the reflective element (618) may be a mirror that reflects light. In another example, the reflective element (618) is a reflective diffuser, that in addition to reflecting the light into the microfluidic chamber (102) and/or light guide (104) also spreads out, or diffuses, the light to further enhance excitation and detection.

Figure 6B:
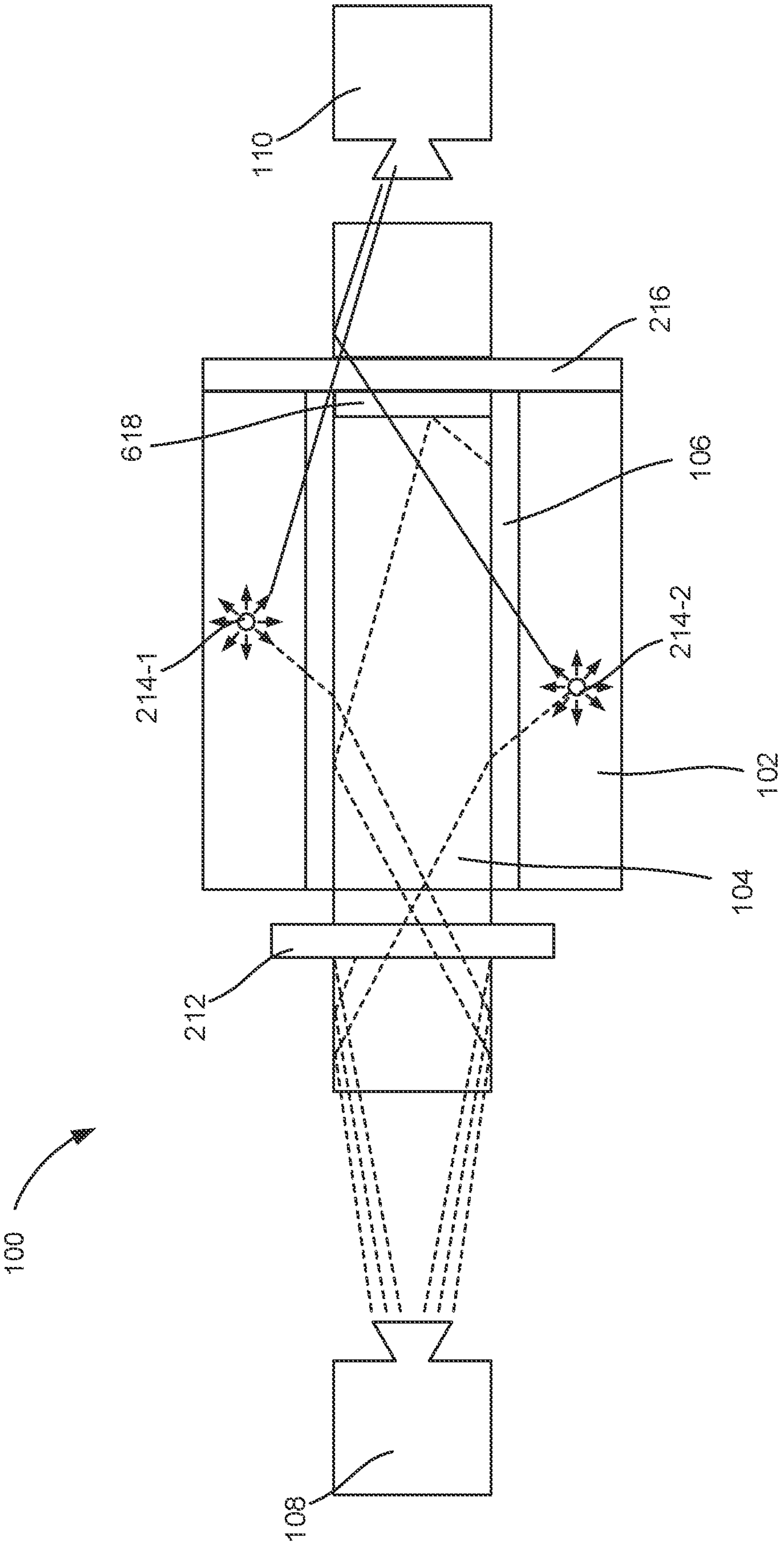

As depicted in FIG. 6B, the emission filter (216) may be a disk filter. Also as depicted in FIG. 6B, the reflective element (618) may be a dichroic mirror. A dichroic mirror may reflect certain wavelengths but not others. As such, the excitation light may reflect back into the microfluidic chamber.

Figure 6C:
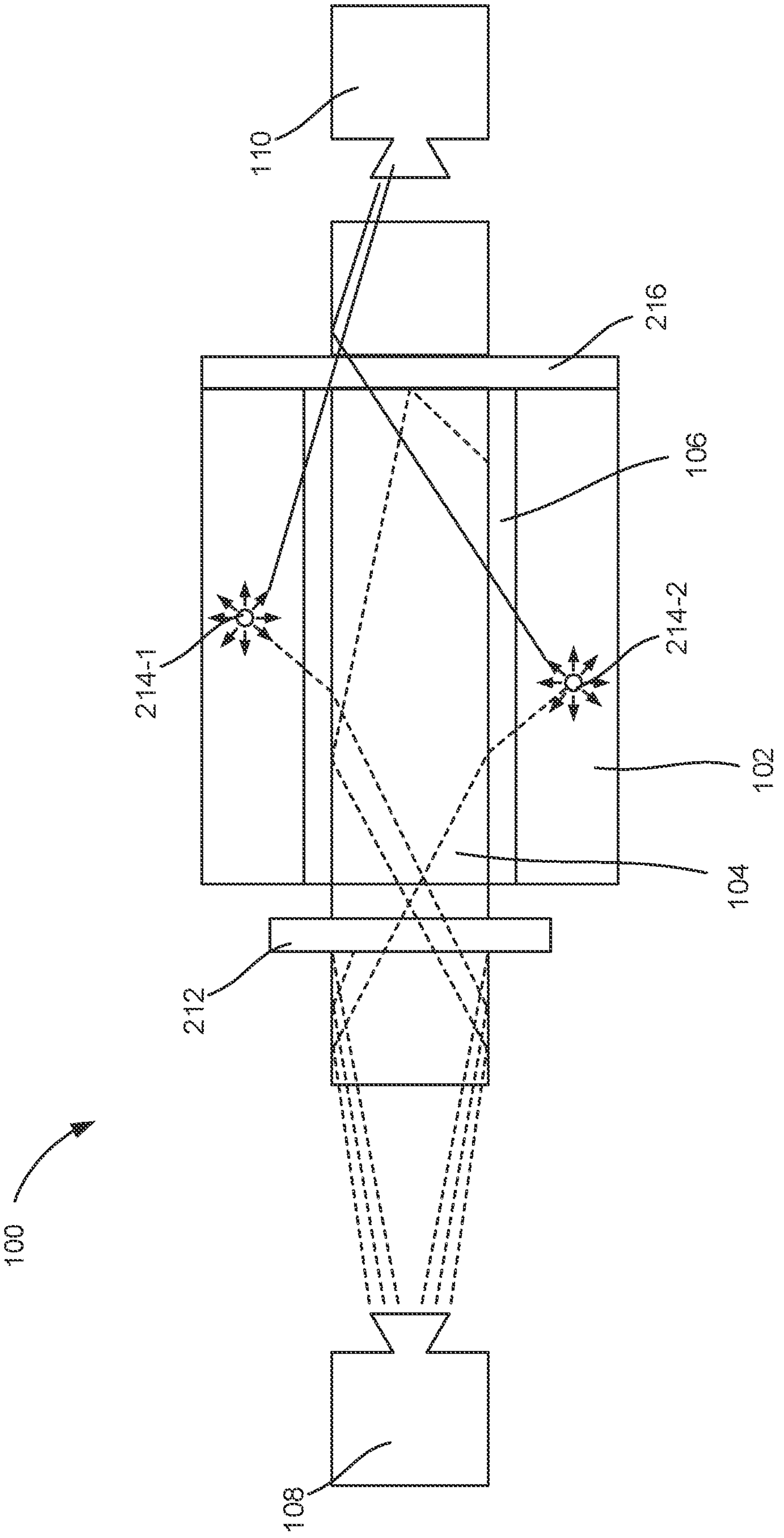

FIG. 6C depicts another example wherein the emission filter (216) is a dichroic filter to reflect excitation light back into the microfluidic chamber (102) while allowing the emission light to pass to the detection system (110). That is, the dichroic filter allows certain light to pass through while reflecting others. As such, rather than just filtering out the excitation light at the emission filter, the excitation light is reflected back into the microfluidic chamber (102) such that it is again available to excite fluorophores within the microfluidic chamber (102), again increasing the light detection operations of the fluorescence detection system (100).

Figure 6D:
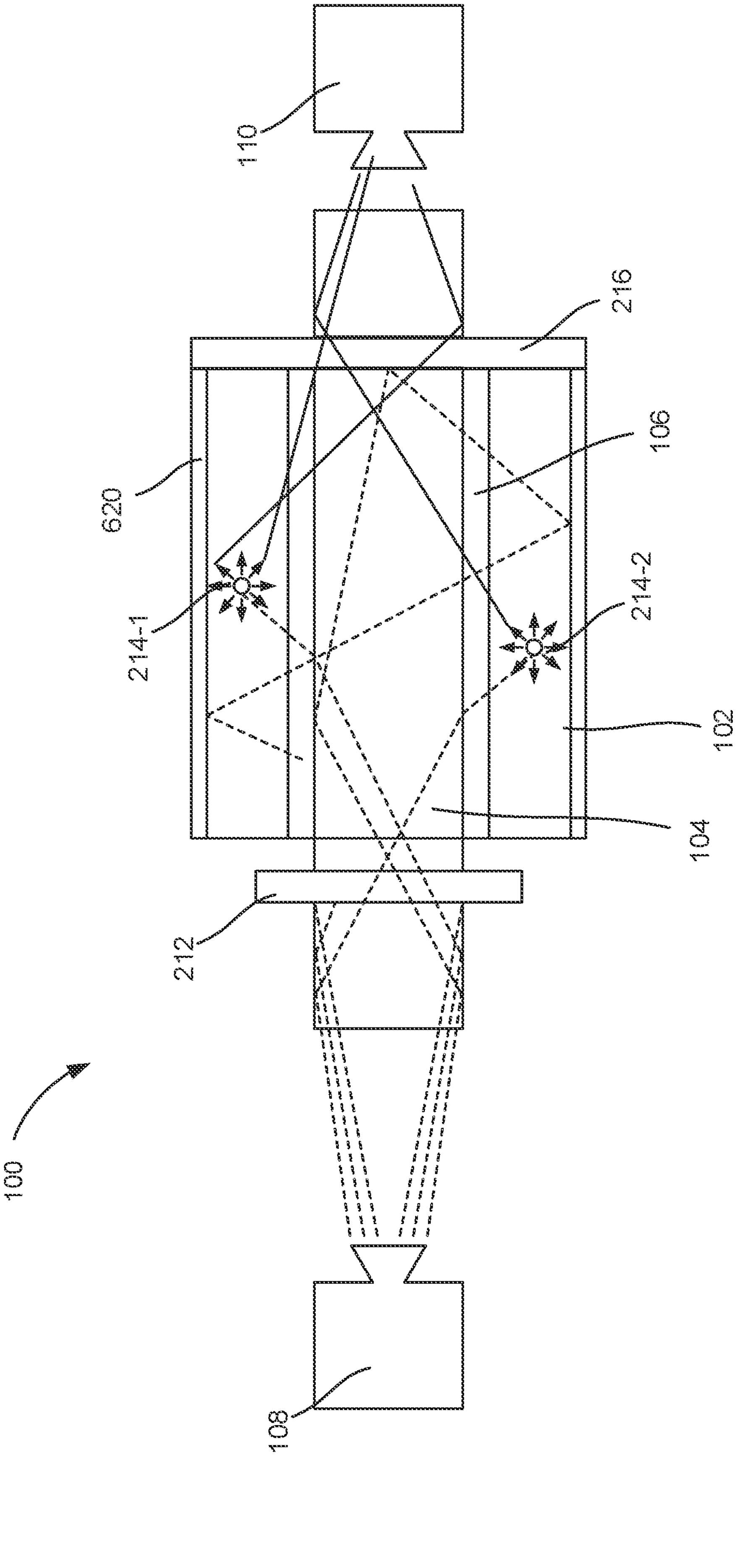

As depicted in FIG. 6D, in some examples, the fluorescence detection system (100) may include a reflective coating (620) on a surface of the microfluidic chamber (102) opposite the light guide (104) to redirect fluorescence towards a center of the fluorescence detection system. That is, as described above, upon excitation, a fluorophore (214) may act as an omnidirectional point source of a longer wavelength emitted light. As it is omnidirectional, some of the emitted light may be lost to the environment and not directed to the detection system (110). In some examples, for example when the microfluidic chamber (102) is exposed to ambient air, the ratio of refractive indices between the air and the microfluidic chamber (102) may be such that the critical angle to trigger total internal reflection will cause a majority of the light to reflect off the surface of the microfluidic chamber (102) back towards a center of the microfluidic chamber (102).

However, under other circumstances, for example when the fluorescence detection system is immersed in another fluid such as water or oil where the refractive index ratio is not as great, the reflective coating (620) may direct more excitation and emission light within the fluorescence detection system (100) rather than being lost through the immersive fluid. As with the reflective element (618), the reflective coating (620) may be a thin film mirror coating, a reflective diffuser, or other type of reflective surface. For these or other reasons, an external surface of the microfluidic chamber (102) may be coated with a reflective coating.

Figure 7A:
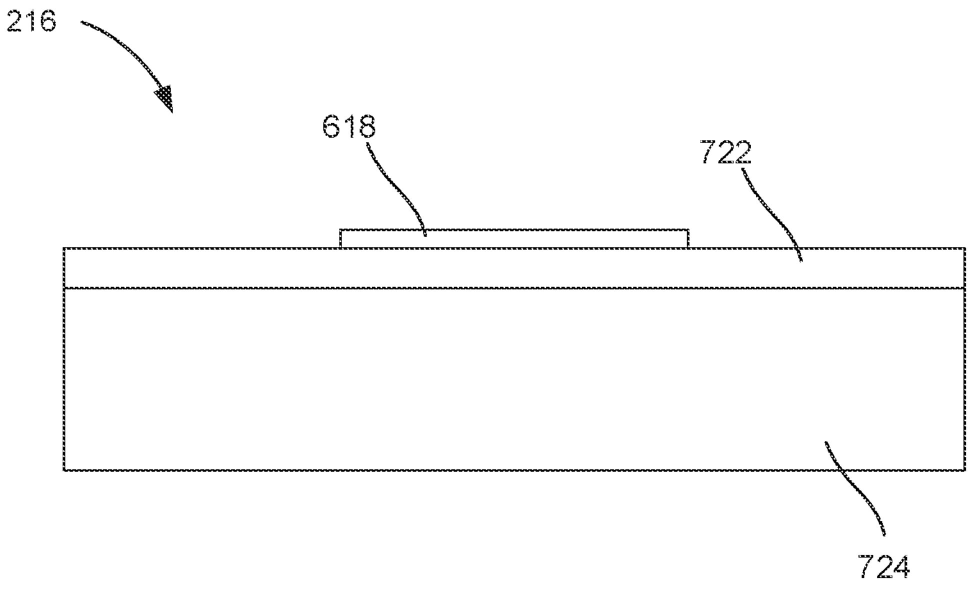
FIGS. 7A and 7B are diagrams of an emission filter of the light guide fluorescence detection system, according to an example of the principles described herein.
Figure 7B:
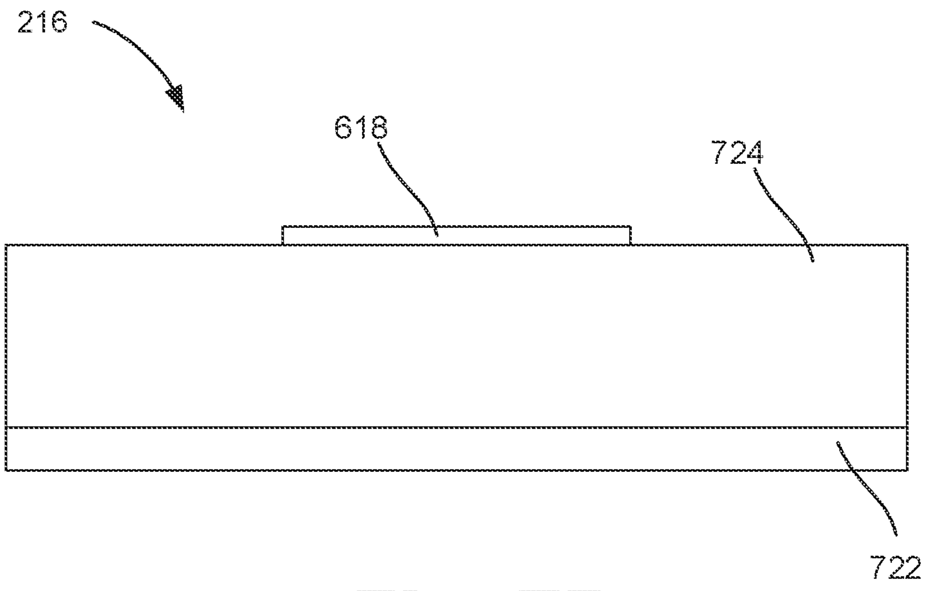

FIGS. 7A and 7B are diagrams of an emission filter (216) of the fluorescence detection system (FIG. 1, 100), according to an example of the principles described herein. As depicted in the examples depicted in FIGS. 7A and 7B, the emission filter (216) may be made up of a number of layers. For example, the emission filter (216) may include a filter substrate (724) which may be an optically transparent material on which a filter material (722) such as a dichroic filter may be placed. FIG. 7A also depicts the reflective element (618) which may be an aluminum thin film mirror, disposed on top of the filter material (722). As depicted in FIG. 7B, a different arrangement may also exist wherein the filter substrate (724) is between the reflective element (618) and the filter material (722).

Figure 8A:
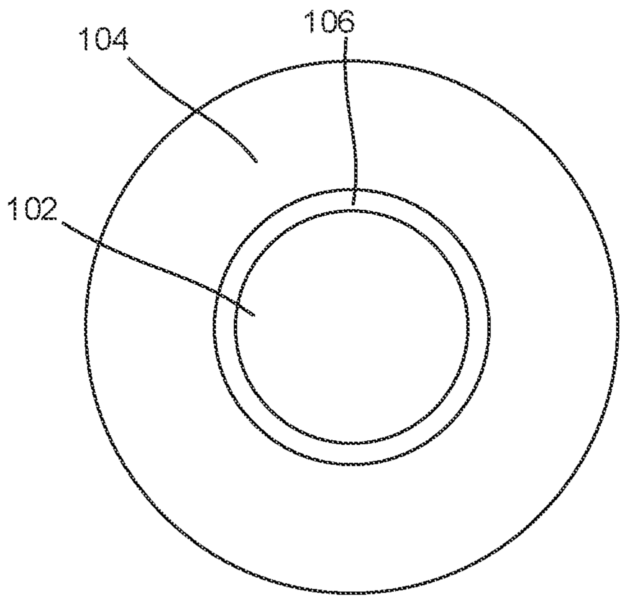
FIGS. 8A and 8B are diagrams of a light guide fluorescence detection system, according to an example of the principles described herein.
Figure 8B:
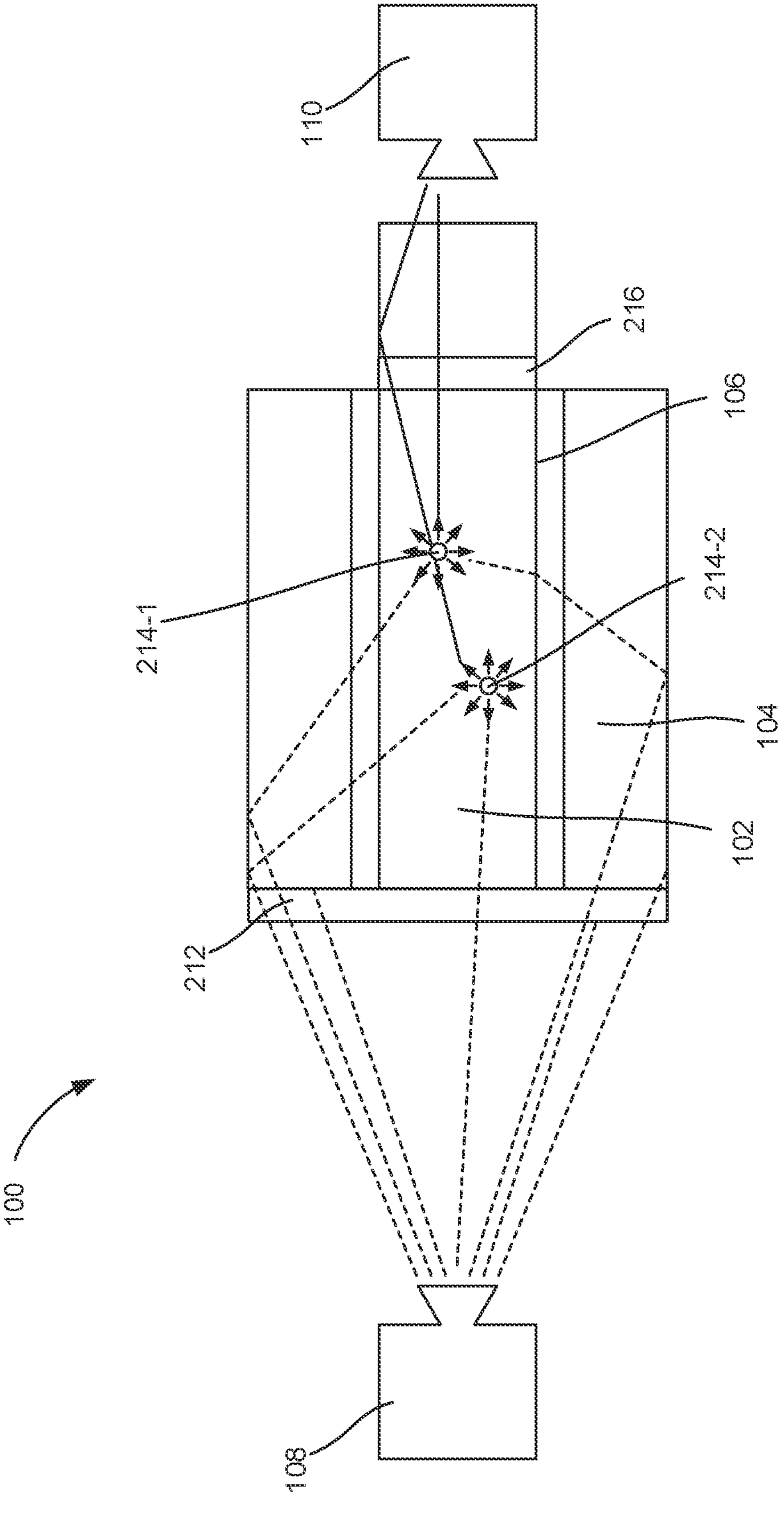

FIGS. 8A and 8B are diagrams of a fluorescence detection system, according to an example of the principles described herein. Specifically, FIGS. 8A and 8B depict a fluorescence detection system (FIG. 1, 100) wherein the light guide (104) surrounds the microfluidic chamber (102). As in other examples described herein, a heating element (106) may be placed between the components. In this example, the heating element (106) surrounds the microfluidic chamber (102) to facilitate maintaining a uniform temperature inside the microfluidic channel (102) based on boundary conditions being maintained at a steady state via control of the heating element (106).

Figure 9A:
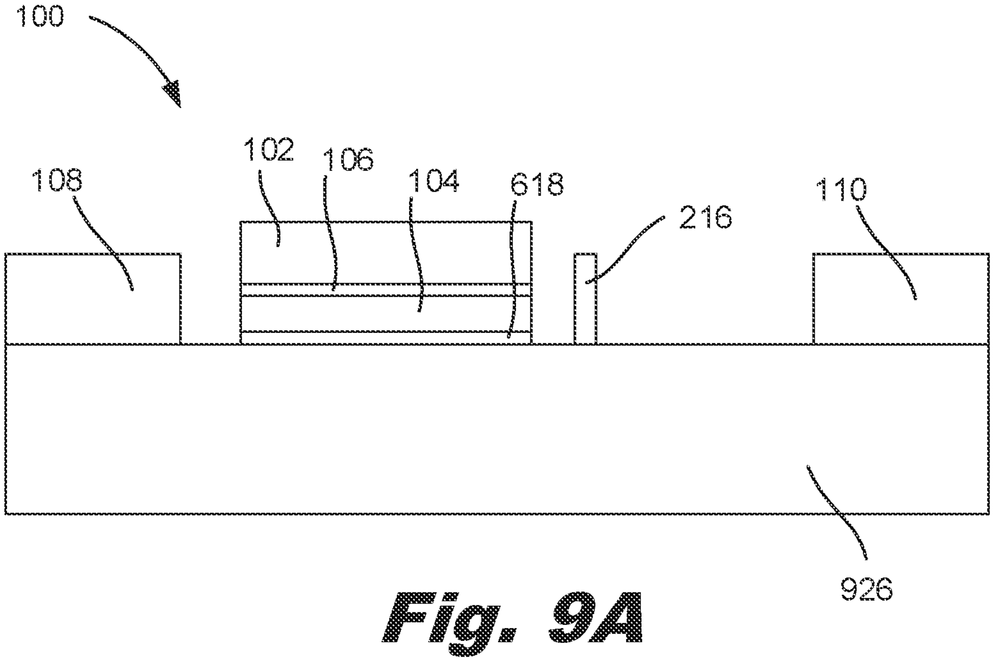
FIGS. 9A and 9B are diagrams of a light guide fluorescence detection system, according to an example of the principles described herein.
Figure 9B:
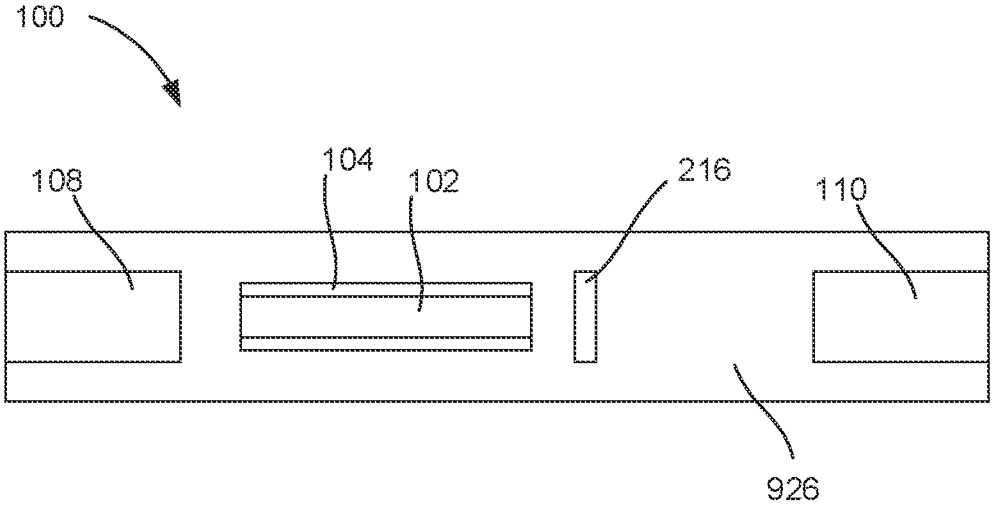

FIGS. 9A and 9B are diagrams of a fluorescence detection system (100), according to an example of the principles described herein. Specifically, FIG. 9A is a side view of the fluorescence detection system (100) and FIG. 9B is a top view of the fluorescence detection system (100). In this example, the microfluidic chamber (102) is adjacent the light guide (104), but is not surrounded by the light guide (104). However, the principles described in connection with FIGS. 9A and 9B may similarly apply to a microfluidic chamber (102) surrounded by a light guide (104).

In this example, the fluorescence detection system (100) further includes a substrate (926) on which the microfluidic chamber (102), light guide (104), heating element (106), illumination source (108), and detection system (110) are disposed. For example, the substrate (926) may be a silicon substrate such as a printed circuit board, glass or an epoxy mold compound or other suitable substrate.

In such an example, a portion of the components may be detachable from other components. For example, the light guide (104), heating element (106), illumination source (108), and detection system (110) may be attached to the substrate while the microfluidic chamber (102) is separable from the light guide (104). In such an example, the microfluidic chamber (102) may be viewed as a disposable cassette. For example, the sample may be loaded into a microfluidic chamber (102), which microfluidic chamber (102) may be transported and plated on top of the light guide in the system for analysis. Following analysis, the microfluidic chamber (102) may be discarded.

Figure 10:
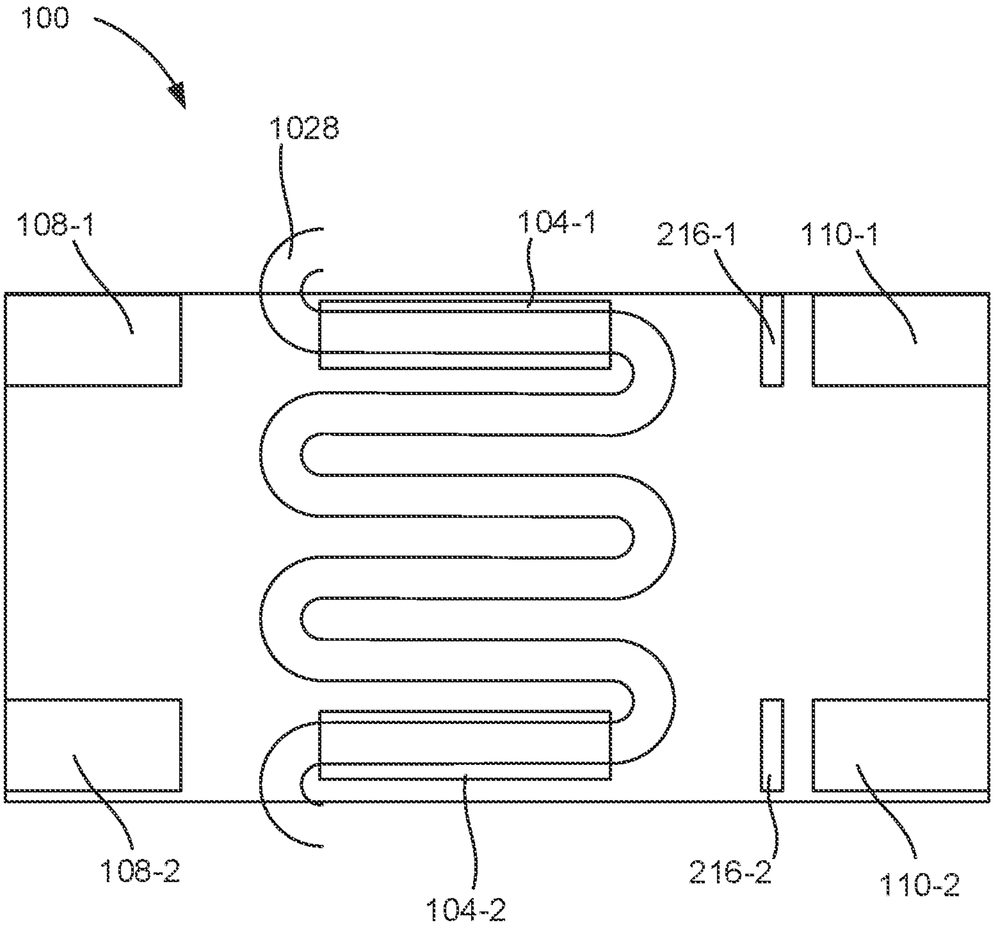
FIG. 10 is a diagram of a light guide fluorescence detection system, according to an example of the principles described herein.

FIG. 10 is a diagram of a fluorescence detection system (100), according to an example of the principles described herein. In this example, the microfluidic chamber (FIG. 1, 102) is a microfluidic channel (1028). In this example, the sample is pumped through the microfluidic channel (1028) as a continuous flow. That is, rather than thermal cycling a static sample, the fluid may be continuously pumped while the fluorescence detection system (100) thermal cycles and heats the sample. With a pump that runs continuously while the temperature cycles in the microfluidic channel (1028), there is a steady stream of processed fluid leaving the microfluidic channel (1028). In this example, the microfluidic channel (1028) may be coupled at one end to a reservoir and an outlet at the other end.

As depicted in FIG. 10, the fluorescence detection system (100) may include multiple instances of elements of the fluorescence detection system (100). For example, the system may include multiple illumination sources (108-1, 108-2), emission filters (216-1, 216-2), and detection systems (110-1, 110-2) which may emit, filter, and detect the same wavelengths of light, for example to verify the measurements of other elements, to provide a time-dependent indication of the reactions, or to monitor the same characteristic of different cycles of the reaction, i.e., different cycles of PCR.

In another example, the elements may emit, filter, or detect different wavelengths in order to track and detect different target compounds. That is, different fluorophores may be excited by different wavelengths of light and may also emit different wavelengths of fluorescence. Accordingly, components with different operating ranges may be able to detect different compounds within a single sample, thus providing multiplexed compound detection in a sample.

Figure 11:
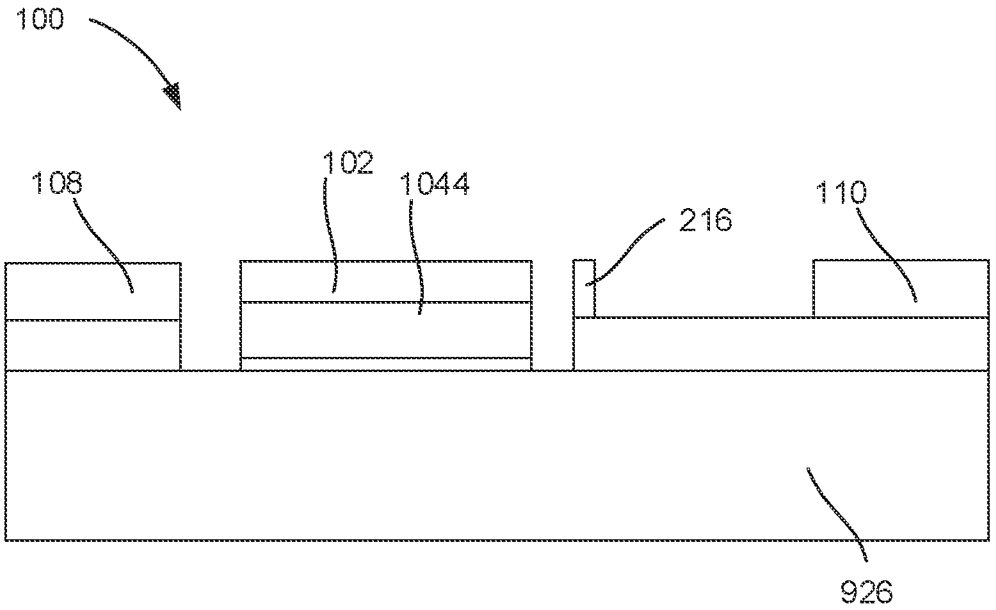
FIG. 11 is a diagram of a light guide fluorescence detection system, according to an example of the principles described herein.

FIG. 11 is a diagram of a fluorescence detection system (100), according to an example of the principles described herein. In the example depicted in FIG. 11, the light guide (104) is disposed vertically on top of the microfluidic chamber (102). In this example, any combination of the light guide (104) and microfluidic chamber (102) may be detachable from components mounted to the substrate (926).

Figure 12:
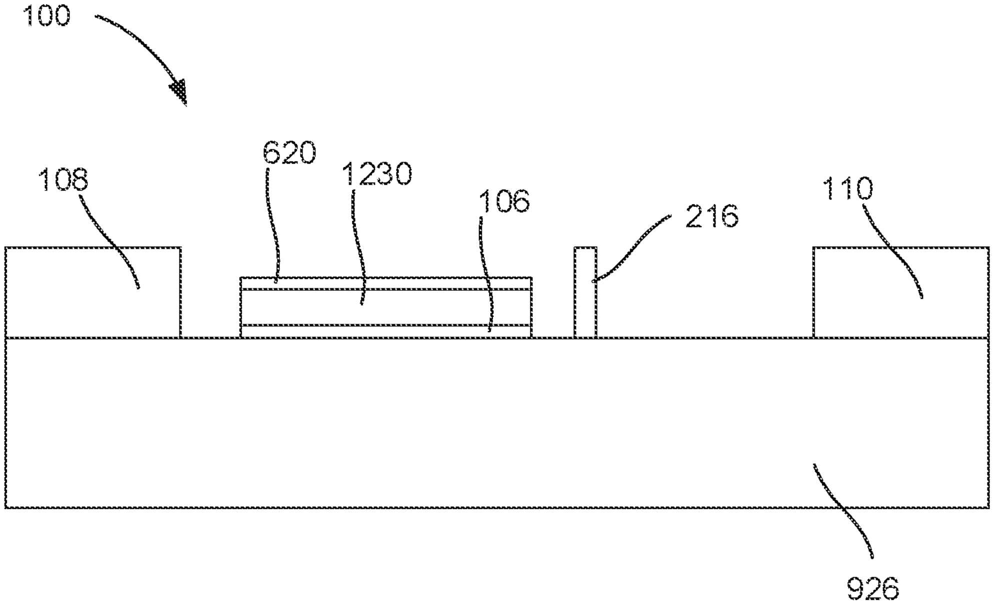
FIG. 12 is a diagram of a light guide fluorescence detection system, according to an example of the principles described herein.

FIG. 12 is a diagram of a fluorescence detection system, according to an example of the principles described herein. In the example of FIG. 12, the microfluidic chamber and the light guide are an integrated structure (1230). That is, the microfluidic chamber may act as a light guide. Note that while each figure depicts different combination of features of the fluorescence detection system (FIG. 1, 100), the different features described herein, such as for example, the microfluidic channel (FIG. 10, 1028), reflective element, ring-shaped dichroic filters and others, may be used any combination.

In summary, such a fluorescence detection system 1) provides a higher signal to noise ratio for compound detection; 2) reduces the computational resources to perform accurate compound detection; 3) provides for faster compound detection to facilitate higher fidelity and faster feedback control; and 4) enables higher speed droplet assays. However, the devices disclosed herein may address other matters and deficiencies in a number of technical areas.

What is claimed is:

1. A fluorescence detection system, comprising:

a microfluidic chamber to receive a sample containing a compound to be detected;

a light guide, a portion of which is adjacent the microfluidic chamber, wherein the light guide:

is to refract excitation light into the microfluidic chamber to excite fluorophores in the microfluidic chamber; and has total internal reflection in portions not adjacent the microfluidic chamber at a lower critical angle as compared to portions adjacent the microfluidic chamber;

a heating element to trigger a reaction in the microfluidic chamber;

an illumination source to provide the excitation light; and a detection system to detect fluorescence generated by the excitation of the fluorophores in the microfluidic chamber.

2. The fluorescence detection system of claim 1, wherein a ratio of refractive indices between the light guide and the microfluidic chamber is 1.05 to 2.5.

3. The fluorescence detection system of claim 1, wherein the microfluidic chamber surrounds the light guide.

4. The fluorescence detection system of claim 3, further comprising a second heating element surrounding the microfluidic chamber.

5. The fluorescence detection system of claim 1, further comprising a reflective coating on a surface of the microfluidic chamber opposite the light guide to redirect fluorescence towards a center of the fluorescence detection system.

6. The fluorescence detection system of claim 1, wherein the light guide surrounds the microfluidic chamber.

7. The fluorescence detection system of claim 1, further comprising a substrate on which the microfluidic chamber, light guide, heating element, illumination source, and detection system are disposed.

8. The fluorescence detection system of claim 7, wherein:

the light guide, heating element, illumination source, and detection system are attached to the substrate; and the microfluidic chamber is separable from the light guide.

9. A method, comprising:

introducing excitation light into a light guide of a fluorescence detection system;

refracting, via the light guide, the excitation light towards a microfluidic chamber having portions adjacent the light guide, wherein the light guide has total internal reflection in portions not adjacent the microfluidic chamber at a lower critical angle as compared to the portions adjacent the microfluidic chamber;

trigger a reaction within the microfluidic chamber by heating a sample within the microfluidic chamber; and monitoring the reaction by detecting, at a detection system, the fluorescence that is indicative of a target compound within the microfluidic chamber.

10. The method of claim 9 wherein:

the microfluidic chamber is a microfluidic channel; and the method further comprises introducing a continuous flow of the sample through the microfluidic channel.

11. The method of claim 9, wherein the light guide and microfluidic chamber are an integrated structure.

12. A fluorescence detection system, comprising:

a longitudinal microfluidic chamber to receive a sample containing a compound to be detected;

a longitudinal light guide having a first portion adjacent the longitudinal microfluidic chamber and a second portion not adjacent the longitudinal microfluidic chamber, wherein the light guide:

is to refract excitation light into the adjacent longitudinal microfluidic chamber along the first portion; and has total internal reflection along the second portion at a critical angle less than a critical angle along the first portion;

a heating element disposed between the longitudinal microfluidic chamber and the longitudinal light guide to trigger a reaction in the longitudinal microfluidic chamber;

an illumination source at one end of the longitudinal microfluidic chamber to provide the excitation light to the longitudinal microfluidic chamber;

an excitation filter between the illumination source and the longitudinal light guide to allow excitation light to pass and to filter light not absorbed by the fluorophores;

a detection system at an opposite end of the longitudinal microfluidic chamber to detect fluorescence generated by the excitation of the compounds in the microfluidic chamber; and an emission filter between the longitudinal light guide and the detection system to allow emission light to pass and filter excitation light.

13. The fluorescence detection system of claim 12, further comprising a reflective element adjacent the emission filter to reflect the excitation light towards the longitudinal microfluidic chamber.

14. The fluorescence detection system of claim 13, wherein:

the reflective element aligns with the longitudinal light guide; and the emission filter is a ring filter surrounding the reflective element.

15. The fluorescence detection system of claim 12, wherein the emission filter is a dichroic filter to reflect excitation light back into the longitudinal microfluidic reaction chamber and allow the emission light to pass to the detection system.

* * * * *